United States Patent

Yoshida et al.

(10) Patent No.: US 6,525,235 B2
(45) Date of Patent: Feb. 25, 2003

(54) METHOD FOR MANUFACTURING 2,6-DIMETHYLNAPHTHALENE

(75) Inventors: Shingo Yoshida, Osaka (JP); Masahiro Motoyuki, Osaka (JP); Tomoki Uemura, Osaka (JP); Koji Yamamoto, Kobe (JP)

(73) Assignee: Kabushiki Kaisha Kobe Seiko Sho (Kobe Steel, Ltd.), Kobe (JP)

( * ) Notice: Subject to any disclaimer, the term of this patent is extended or adjusted under 35 U.S.C. 154(b) by 0 days.

(21) Appl. No.: 09/965,822

(22) Filed: Oct. 1, 2001

(65) Prior Publication Data

US 2002/0065447 A1 May 30, 2002

(30) Foreign Application Priority Data

Oct. 2, 2000 (JP) ........................................ 2000-302601

(51) Int. Cl.[7] ................................................. C07C 7/14
(52) U.S. Cl. ........................ 585/814; 585/812; 585/815; 585/816; 585/817
(58) Field of Search ................................ 585/812, 814, 585/815, 816, 817

(56) References Cited

U.S. PATENT DOCUMENTS

| | | | |
|---|---|---|---|
| 5,723,711 A | 3/1998 | Motoyuki et al. | 585/481 |
| 5,744,670 A | 4/1998 | Motoyuki et al. | 585/320 |
| 6,011,190 A | 1/2000 | Motoyuki et al. | 585/323 |
| 6,018,086 A | 1/2000 | Motoyuki et al. | 585/323 |
| 6,018,087 A | 1/2000 | Motoyuki et al. | 585/481 |
| 6,121,501 A | 9/2000 | Motoyuki et al. | 585/323 |
| 6,153,808 A | 11/2000 | Motoyuki et al. | 585/821 |

FOREIGN PATENT DOCUMENTS

| | | |
|---|---|---|
| EP | 0 939 068 | 9/1999 |
| JP | 48-5767 | 1/1973 |
| JP | 48-22449 | 3/1973 |
| JP | 50-22553 | 7/1975 |

OTHER PUBLICATIONS

Derwent Publications, AN 1975–58020W. JP 50–022553, Jul. 31, 1975.

*Primary Examiner*—Walter D. Griffin
*Assistant Examiner*—Tam M. Nguyen
(74) *Attorney, Agent, or Firm*—Oblon, Spivak, McClelland, Maier & Neustadt, P.C.

(57) ABSTRACT

The present invention provides a method for manufacturing a highly pure 2,6-dimethylnaphthalene having a purity of 99% or more even when a mixture of dimethylnaphthalene isomers containing 5 wt % or more of 2,7-dimethylnaphthalate is used as a feedstock. The method for manufacturing 2,6-dimethylnaphthalene comprises a step of performing crystallization and solid-liquid separation of a liquid primarily containing dimethylnaphthalene isomers so that the liquid is separated into a cake containing the dimethylnaphthalene isomers and a mother liquor, and a step of performing separation/purification of the cake. In the method described above, the crystallization and the solid-liquid separation are performed under the condition in which the ratio of the content of 2,6-dimethylnaphthalene in the mother liquor to that of 2,7-dimethylnaphthalene therein is not less than 1 so that the content of 2,6-dimethylnaphthalene in the cake is 60% or more and that the content of 2,7-dimethylnaphthalene therein is 6.5% or less. As a result, a highly pure 2,6-dimethylnaphthalene is obtained by performing the separation/purification of the cake.

4 Claims, 7 Drawing Sheets

METHOD FOR MANUFACTURING 2,6-DIMETHYLNAPHTHALENE

BACKGROUND OF THE INVENTION

1. Field of the Invention

The present invention relates to a method for manufacturing 2,6-dimetylnaphthalene which can be used effectively as a feedstock for a monomer such as 2,6-naphthalene dicarboxylic acid which is used for forming polyesters such as polyethylene naphthalate.

2. Description of the Related Art

In order to obtain the superior features of polyethylene naphthalate which is used for manufacturing fibers, films, and the like, it is necessary that 2,6-naphthalene dicarboxylic acid, which is a monomer for forming polyethylene naphthalate, has a high purity, and accordingly, it is also desirable that 2,6-dimethylnaphtahlene which is a precursor therefor has a high purity. Dimethylnaphthalene (hereinafter referred to as "DMN") has 10 isomers, and a highly pure 2,6-dimethylnaphthalene (preferably having a purity of 99% or more), which is mixed with substantially none of the other 9 isomers, is preferably used for forming 2,6-naphthalene dicarboxylic acid.

As a method for manufacturing the 2,6-DMN described above, there may be mentioned a method of separating 2,6-DMN from a mixture obtained by isomerizing 1,5-DMN which is formed by a reaction between orthoxylene and butadiene; a method of separating 2,6-DMN from a mixture obtained by disproportionating methyl naphthalene or isomerizing dimethylnaphthalenes and a method of separating 2,6-DMN from a tar or an oil fraction. However, the fractions and the mixtures described above are each a mixture containing many types of DMN isomers in addition to 2,6-DMN, and hence, the 2,6-DMN must be separated from the mixture described above. However, since the boiling points of these DMN isomers are very close to each other, it has been difficult to separate a highly pure 2,6-DMN therefrom by distillation which is commonly used for separation/purification of organic compounds.

Accordingly, as a method for separating 2,6-DMN, a crystallization method or an adsorption method has been proposed, and in addition to these methods mentioned above, a method comprising steps of forming a complex by using a certain organic compound, separating the complex, and decomposing the separated complex, and combinations of the methods described above have also been proposed. A cooling crystallization method is a method exploiting the property of 2,6-DMN having a highest melting point among the 10 types of DMN isomers, and since the cooling crystallization method is simple compared to the methods described above, this method can be used suitably as an industrial separation method. However, since it has been difficult to obtain a 2,6-DMN having a purity of 99% or more only by the cooling crystallization method, a process such as treatment using a solvent is generally used together therewith. For example, in Japanese Unexamined Patent Application Publication Nos. 48-5767 and 48-22449, and Japanese Examined Patent Application Publication No. 50-22553, a method has been disclosed in which after a mixture of DMN isomers is crystallized by cooling, solid-liquid separation was performed by suction filtration, and the obtained solid component is dissolved in a solvent and is then crystallized by cooling. However, in the method disclosed in the publications described above, the mixture of DMN isomers used as a feedstock primarily contains specific DMN isomers among the 10 types of isomers, such as 2,6-DMN, 1,6-DMN, and 1,5-DMN, which are easily isomerized to each other and are easily separated, and the content of 2,7-DMN which is difficult to separate from 2,6-DMN is limited to less than 5 mole percent (approximately equivalent to 5 wt) or less. A mixture of DMN isomers obtained in a typical manufacturing process generally contains 5 wt % or more of 2,7-DMN, and hence, when the mixture of DMN isomers containing 5 wt % or more of 2,7-DMN is used as a feedstock in accordance with the related art disclosed in the publications described above, it has been difficult to obtain a highly pure 2,6-DMN.

SUMMARY OF THE INVENTION

In view of the problems described above, the present invention was made, and an object of the present invention is to provide a method for manufacturing a 2,6-DMN having a purity of 99% or more even when a mixture of DMN isomers containing 5 wt % or more of 2,7-DMN is used as a feed stock.

To this end, a method for manufacturing 2,6-dimethylnaphthalene according to the present invention comprises a step of performing at least one crystallization and at least one solid-liquid separation of a liquid primarily containing dimethylnaphthalene isomers used as a feedstock so that the liquid is separated into a cake containing dimethylnaphthalene isomers and a mother liquor, and so that the content of 2,6-dimethylnaphthalene is increased in the cake; and a step of performing separation/purification of the cake. In the method described above, the crystallization and the solid-liquid separation are performed under the condition in which the ratio of the content of 2,6-dimethylnaphthalene in the mother liquor to that of 2,7-dimethylnaphthalene therein (hereinafter referred to as "ratio 2,6-DMN/2,7-DMN" in some cases) is not less than 1 so that the content of 2,6-dimethylnaphthalene in the cake is 60% or more and that the content of 2,7-dimethylnaphthalene therein is 6.5% or less, whereby a 2,6-dimethylnaphthalene having a purity of 99% or more is obtained by performing the separation/purification of the cake.

According to the method of the present invention described above, a highly pure 2,6-DMN can be manufactured even when the mixture containing dimethylnaphthalene isomers contains 5 wt % or more of 2,7-dimethylnaphthalene is used as a feedstock.

In addition, in the step of performing the crystallization and the solid-liquid separation described above, it is preferable that after cooling crystallization is performed, press filtration be performed as the solid-liquid separation.

In the present invention, "%" means "wt %".

DESCRIPTION OF THE PREFERRED EMBODIMENTS

Figure 1:
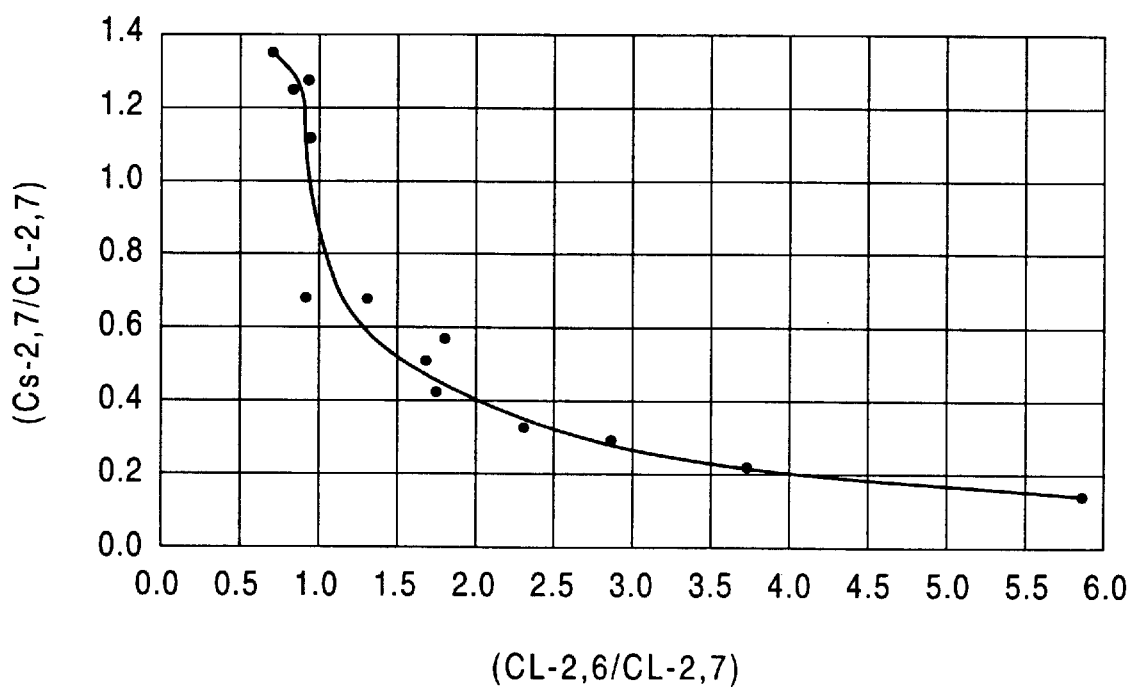
FIG. 1 is a graph showing the relationship between the content ratio 2,6-DMN/2,7-DMN (CL-2,6/CL-2,7) in a mother liquor and the ratio of the content of the 2,7-DMN in a cake containing DMN isomers to that of the 2,7-DMN (Cs-2,7/CL-2,7) in the mother liquor.

It has been know that 2,6-DMN and 2,7-DMN form a eutectic crystal at a ratio 2,6-DMN/2,7-DMN of 0.7. Accordingly, in order to increase the recovery rate of 2,6-DMN, in a conventional cooling crystallization step, the feedstock is cooled so that the ratio 2,6-DMN/2,7-DMN in a mother liquor becomes approximately 0.7, and the material containing crystals thus formed is separated and purified (for example, recrystallization such as a high pressure crystallization method or treatment using a solvent). However, it was found by the inventors of the present invention that even when the material containing crystals thus formed was condensed by an effective solid-liquid separation method such as press filtration so that 60 wt % or more of 2,6-DMN was contained in the solid phase component, approximately 10 wt % of 2,7-DMN was also contained therein, and hence, it was difficult to obtain a 2,6-DMN having a purity of 99% or more by performing separation/purification of the solid phase component described above. In addition, through intensive research by the inventors of the present invention on the method for manufacturing a high purity 2,6-DMN having a purity of 99% or more, it was found that a reduction of the content of the 2,7-DMN contained in the solid phase component is important before the separation/purification was performed.

Furthermore, it was also found that even when the ratio 2,6-DMN/2,7-DMN in the mother liquor was 0.7 or more, since 2,7-DMN in a solid state is present in the solid phase component, in order to reduce the content of the 2,7-DMN in the solid phase component by crystallization, it was important that the crystallization condition for the mixture be appropriately controlled based on understanding of the behavior of the 2,7-DMN. Through intensive research by the inventors of the present invention on the behavior of the 2,7-DMN, it was discovered that the behavior of the 2,7-DMN could be systematically understood by the ratio 2,6-DMN/2,7-DMN in the mother liquor, and as a result, the present invention was made. Hereinafter, the present invention will be described in detail.

A feedstock used in the present invention is not specifically limited as long as the feedstock is a mixture primarily composed of dimethylnaphthalene isomers including 2,6-DMN and is required to be separated and purified.

When crystallization and solid-liquid separation are performed for the feedstock described above, a solid phase component (hereinafter referred to as "cake containing DMN isomers) and a liquid (hereinafter referred to as "mother liquor") are obtained, and in the steps described above, the crystallization and the solid-liquid separation are preferably performed so that the ratio of the content of the 2,6-DMN in the mother liquor to that of the 2,7-DMN therein is not less than 1.0.

That is, when the crystallization and the solid-liquid separation are performed under the condition in which the ratio of the content of the 2,6-DMN to that of the 2,7-DMN in the mother liquor is not less than 1.0, it is preferable since the content of the 2,7-DMN in the obtained cake containing DMN isomers can be 6.5% or less. Accordingly, when a cake containing DMN isomers including 6.5% or less of 2,7 DMN is separated and purified, a 2,6-DMN having a purity of 99% or more can be obtained. In addition, in order to obtain a highly pure 2,6-DMN, the content of the 2,7-DMN in the cake is preferably 6.5% or less and is more preferably 6.0% or less.

FIG. 1 is a graph showing the relationship between the content ratio 2,6-DMN/2,7-DMN (CL-2,6/CL-2,7) in the mother liquor and the ratio (Cs-2,7/CL-2,7) of the content of the 2,7-DMN in the cake containing DMN isomers to that of the 2,7-DMN in the mother liquor. Since 2,6-DMN and 2,7-DMN have similar molecular structures, properties, and behaviors to each other, a 2,7-DMN in a solid state may be present in the cake containing DMN isomers in many cases after solid-liquid separation is performed. As shown in FIG. 1, when the content ratio 2,6-DMN/2,7-DMN (CL-2,6/CL-2,7) in the mother liquor is less than 1.0, the ratio (Cs-2,7/CL-2,7) of the content of the 2,7-DMN in the cake containing DMN isomers to that of the 2,7-DMN in the mother liquor is more than 1.0, and it is understood that the content of the 2,7-DMN in the cake containing DMN isomers is larger than that in the mother liquor. Accordingly, in order to reduce the content of the 2,7-DMN in the cake containing DMN isomers, the content ratio 2,6-DMN/2,7-DMN (CL-2,6/CL-2,7) in the mother liquor is preferably 1.0 or more, is more preferably 1.2 or more, and is even more preferably 1.5 or more.

Since the crystallization condition depends on the composition of the feedstock, in order to make the content ratio 2,6-DMN/2,7-DMN in the mother liquor 1.0 or more, in accordance with the contents of the 2,6-DMN, 2,7-DMN, and the like in the feedstock, the crystallization conditions such as a temperature may be appropriately controlled. For example, as for a crystallization temperature, the solid phase composition and the liquid phase composition are first obtained based on solid-liquid equilibrium, and an appropriate operation temperature may be determined on the material balance between the two phases.

In the present invention, the feedstock to be crystallized may contain 5% or more of 2,7-DMN; however, at the same time, 10% or more of 2,6-DMN is preferably contained. When the content of the 2,6-DMN in the feedstock is less than 10%, it is preferable that the feedstock be processed by distillation or the like so as to increase the content of the 2,6-DMN to 10% or more and be then crystallized.

According to the present invention, a 2,6-DMN having a purity of 99% or more can be easily obtained by steps of crystallizing the feedstock, performing solid-liquid separation for the slurry obtained by the previous step to obtain a cake containing DMN isomers and a mother liquor, and performing separation/purification of the cake.

The "crystallization" in the present invention means that a solid phase (crystal) is precipitated from the feedstock. As the crystallization method, various methods, such as physical crystallization methods using cooling, solvent evaporation, or pressure, may be used; however, in the present invention, a cooling crystallization method is preferably used which is simplest and is used suitably as an industrial separation method. When the cooling crystallization method is used, since the slurry containing crystals obtained by the cooling crystallization method contains many DMN isomers and other alkylnaphthalenes in a liquid state (partly in a solid state) as impurities in addition to 2,6-DMN, the slurry containing the crystals is preferably separated into a solid (cake containing DMN isomers) and a liquid (mother liquor) by solid-liquid separation.

In addition, the "solid-liquid separation" in the present invention means that a slurry containing crystals obtained by crystallizing the feedstock is separated into a solid phase component and a liquid phase component, and as the solid-liquid separation method, various methods, such as pressure filtration, press filtration, or suction filtration, may be mentioned by way of example. However, when the cake containing DMN isomers obtained by solid-liquid separation contains a large amount of impurities, it is difficult to obtain a highly pure 2,6-DMN even by a subsequent separation/purification step, and hence, it is particularly preferable that press filtration be used in the present invention.

Since the higher the pressure during press filtration, the better the separation effect is, the pressure is preferably 2 MPa or more, is more preferably 5 MPa or more, and is even more preferably 8 MPa or more. As the press filtration method, a tube press, a filter press, a plate press, a cage press, a belt press, a screw press, a disc press method, and the like may be mentioned by way of example. Among these methods mentioned above, a method which can perform press filtration at a higher pressure is preferable when used for industrial mass production, and above all, the tube press method is preferably used in which a high pressure of 10 MPa or more can be applied.

In the present invention, the content of the 2,6-DMN in the cake containing DMN isomers is preferably 60% or more after solid-liquid separation is performed, and is more preferably 80% or more. When the content is 60% or more, the impurities in a liquid state present in the cake can be easily removed by a step of separation/purification described below, and a highly pure 2,6-DMN having a purity of 99% or more can be finally obtained. In contrast, when the content of the 2,6-DMN is less than 60%, it is not preferable since the recovery rate of the 2,6-DMN may be decreased in some cases after the step of separation/purification is performed, or the purity thereof may be decreased in some cases when the recovery rate is maintained at a certain level.

In addition, since the DMN isomers other than 2,6-DMN and 2,7-DMN and the alkylnaphthalenes in a liquid state serve as a solvent to dissolve the 2,7-DMN in a solid state.

Therefore, if the content of the 2,6-DMN in the cake is 60% or more, and the content of the 2,7-DMN therein is 6.5% or less, it is preferable condition since the 2,7-DMN can be easily removed together with the impurities in a liquid state.

In the case in which a cake containing 60% or more of 2,6-DMN cannot be obtained by one crystallization step and one solid-liquid separation step (hereinafter referred to as "single stage" in some cases), the crystallization and the solid-liquid separation are preferably repeated (hereinafter referred to as "multistage" in some cases) so as to increase the content of the 2,6-DMN to 60% or more.

Figure 7A:
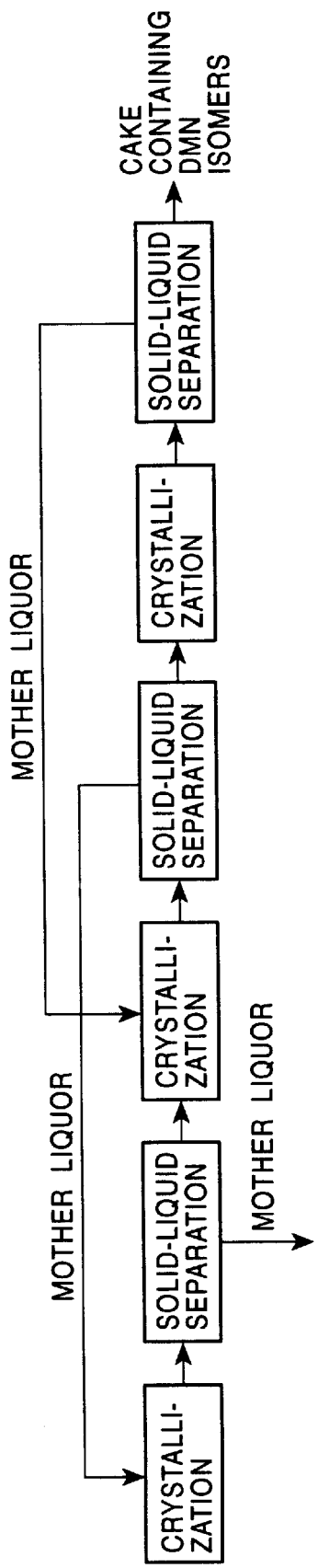
FIG. 7A is a view showing a step to which a mother liquor is recycled by way of example.

In order to increase the content of the 2,6-DMN in the cake containing DMN isomers and to increase the final recovery yield of the 2,6-DMN, the crystallization and the solid-liquid separation are preferably performed in a multistage manner, i.e., are preferably each performed at least two times (two stages). When the solid-liquid crystallization step is repeatedly performed, it is not always necessary that the same solid-liquid crystallization method be repeated. In addition, when the cooling crystallization and the solid-liquid separation are repeatedly performed, a mother liquor obtained by the solid-liquid separation at the second stage or at a subsequent stage is preferably returned to a stage preceding the stage at which the mother liquor is obtained in order to increase the recovery rate of the 2,6-DMN (see FIG. 7A).

Figure 7B:
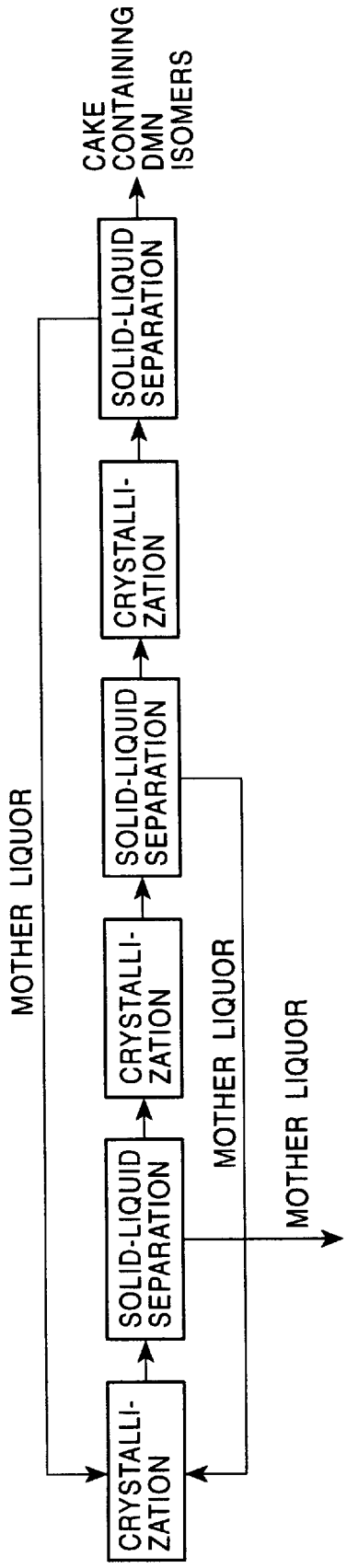
FIG. 7B is a view showing a step to which a mother liquor is recycled by way of example.

In addition, when the crystallization and the solid-liquid separation are repeatedly performed, a mother liquor is preferably returned to the preceding stage at which the mother liquor is obtained; however, the mother liquor may be processed by the crystallization and the solid-liquid separation at a stage other than the preceding stage described above (see FIG. 7B).

The cake containing DMN isomers obtained by the solid-liquid separation is processed by separation/purification so as to manufacture a highly pure 2,6-DMN, and the "separation/purification" in the present invention means that a highly pure 2,6-DMN is obtained by separating and removing impurities other than 2,6-DMN from the cake containing DMN isomers, i.e., from the solid phase component. As the separation/purification method, for example, a high pressure crystallization method or solvent-washing method, may be mentioned. In the case of the solvent-washing method, the separation/purification may be performed by steps of, for example, washing a cake containing DMN isomers fed into a solvent, performing solid-liquid separation of the slurry containing crystals formed in the washing step by a typical method using a centrifuge or the like, and removing the solvent from the solid phase component thus obtained by distillation or the like, whereby a highly pure 2,6-DMN can be obtained. In addition, in the case described above, a solvent generally used for solvent-washing may be used and is not specifically limited; however, for example, an aliphatic hydrocarbon having 5 to 10 carbons and/or an alicyclic hydrocarbon are preferably used.

Figure 2:
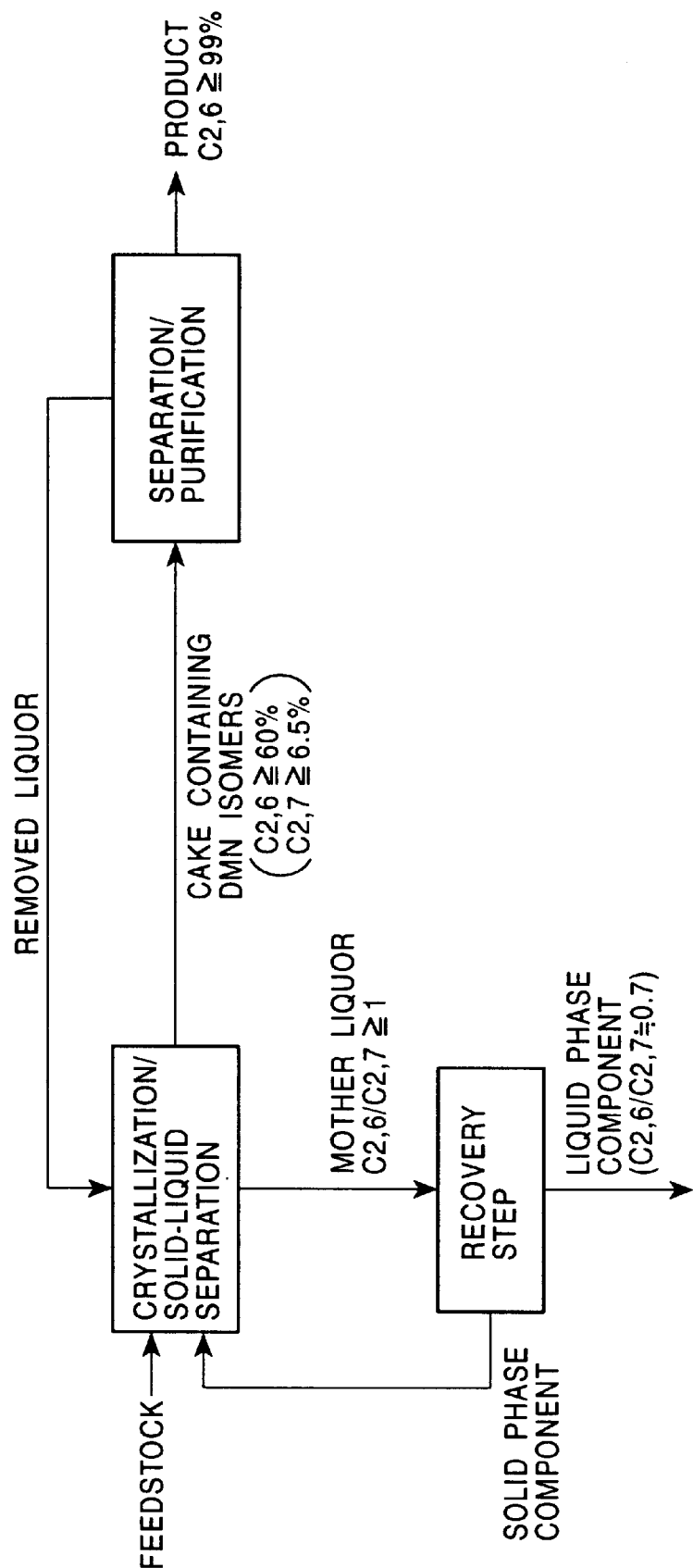
FIG. 2 is a view showing a typical example of a manufacturing process according to the present invention.

FIG. 2 is a view for illustrating a typical example of a manufacturing process according to the present invention. In order to obtain a 2,6-DMN having a purity of 99% or more by separation/purification, the content of the 2,6-DMN (C2,6) and the content of the 2,7-DMN (C2,7) in the cake containing DMN isomers obtained by crystallization and solid-liquid separation are preferably 60% or more and 6.5% or less, respectively. Accordingly, the content ratio 2,6-DMN/2,7-DMN (C2,6/C2,7) in the mother liquor obtained by the crystallization and the solid-liquid separation is preferably 1.0 or more, and in addition, when necessary, it is preferable that the crystallization and the solid-liquid separation be repeatedly performed. In order to increase the recovery rate of the 2,6-DMN (product), it is preferably recommended that the mother liquor be returned to a recovery step (for example, returned to a centrifuge) so as to be separated into a solid phase component and a liquid phase component, and that the solid phase component thus obtained be again processed by the crystallization and the solid-liquid separation. In addition, a mixture (removed liquor) containing DMN isomers obtained by the separation/purification may be again processed by the crystallization and the solid-liquid separation.

Figure 3:
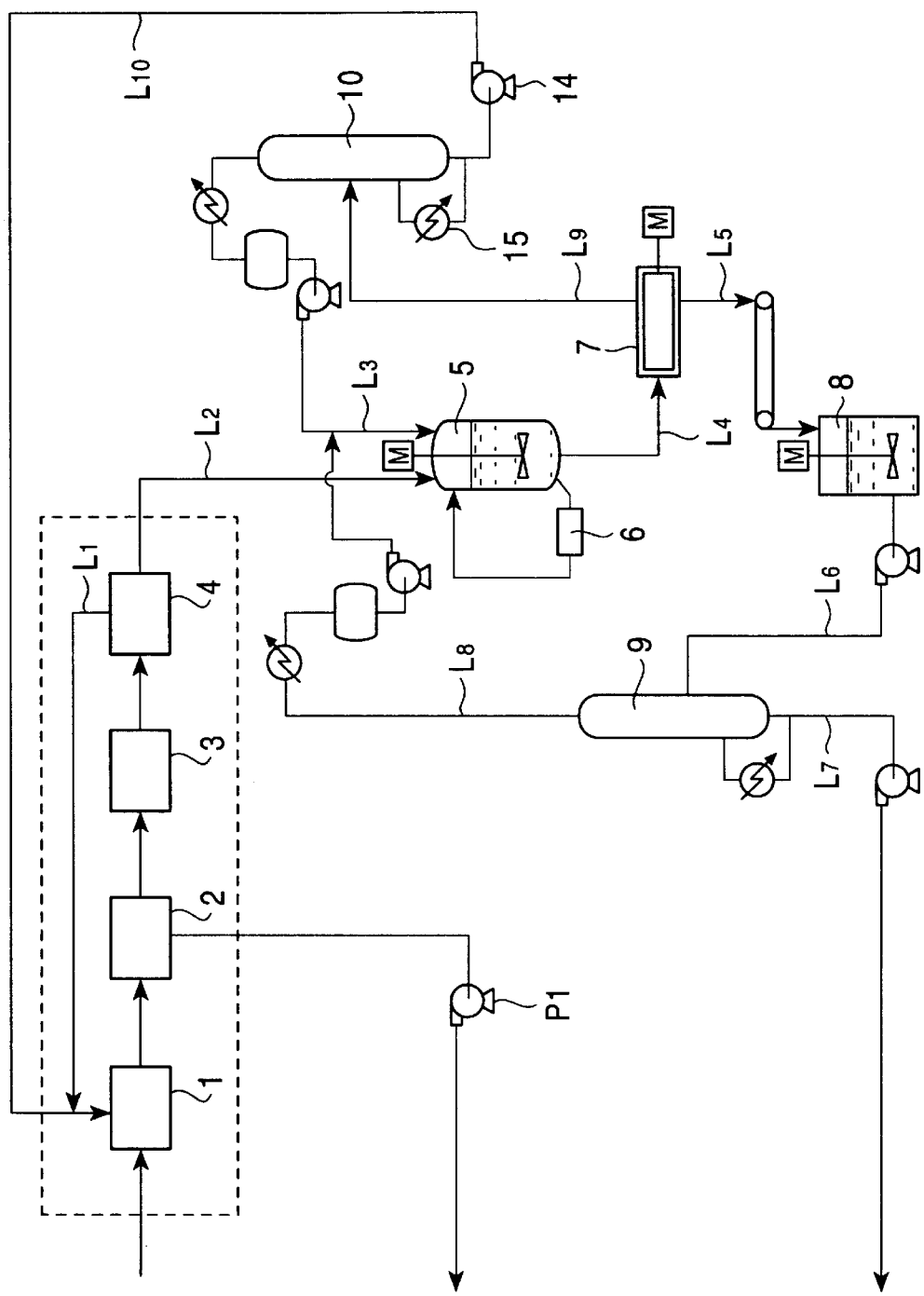
FIG. 3 is a schematic view illustrating a typical example of a method according to the present invention.

FIG. 3 is a schematic view for illustrating the case by way of example in which two stages of crystallization and solid-liquid separation are provide, and in addition, a solvent-washing method is employed for separation/purification; however, the present invention is not limited thereto, and modifications may be made without departing from the scope and the sprit of the present invention. Hereinafter, the present invention will be described with reference to FIG. 3.

A mixture containing DMN isomers used as a feedstock is fed into a first cooling crystallization device 1. In this cooling device 1, the feedstock is cooled to a temperature below the melting point of 2,6-DMN and is then supplied to a first press filtration device 2. The first slurry containing crystals formed by the cooling is processed by solid-liquid separation in this device, and the first mother liquor obtained in this step is supplied outside the production line or is supplied to another step (not shown). The first cake containing DMN isomers formed from the first slurry is supplied to a second cooling crystallization device 3 and is then crystallized (a second slurry containing crystals) by cooling as in the first stage, and subsequently, solid-liquid separation was performed in a second press filtration device 4. The second mother liquor obtained in this step is returned to the first cooling crystallization device 1 via a line $L_1$. In addition, the second cake containing DMN isomers formed from the second slurry is supplied to a washing bath 5 via a line $L_2$. This cake is mixed with a solvent supplied to the washing bath 5 via a line $L_3$ and is washed while stirred. During washing by stirring, the cake and the solvent in the washing bath are adequately supplied to a wet-type pulverizer 6 equipped outside the washing bath, and the cake is pulverized and is then returned to the washing bath 5. The slurry obtained by washing with stirring is supplied to a subsequent solid-liquid separation step 7 via a line $L_4$. In this step, a centrifuge is used by way of example; however, another solid-liquid separation method may also be used. The cake containing 2,6-DMN, which is a solid phase component formed by the centrifuge, is supplied to a melting bath 8 via a line $L_5$, and after melting, the molten cake is separated into a solvent component and a product, i.e., a highly pure 2,6-DMN, by a distillation tower 9. The highly pure 2,6-DMN in the form of a cake thus obtained is recovered as a product via a line $L_7$. The solvent is returned from the distillation tower 9 to the washing bath 5 via a line $L_8$ and the line $L_3$. In addition, the solvent separated in the solid-liquid separation step 7 is supplied to a distillation tower 10 via a line $L_9$ and is then separated into a solvent component and a mixture containing DMN isomers. The solvent component mentioned above is returned to the washing bath 5 via the line $L_3$, and the mixture containing DMN isomers (removed liquor) is returned to the first cooling crystallization device 1 via a line $L_{10}$.

Hereinafter, the present invention will be described in more detail with reference to examples; however, the present invention is not limited thereto, and modifications may be made without departing from the sprit and the scope of the present invention. In the examples and comparative examples described below, "%" means "wt %". In addition, as "impurities" shown in tables, methylnaphthalene, ethylnaphthalene, hydrocarbons each having a boiling point equivalent to those of DMN's, and the like may be mentioned.

EXAMPLES

First Example

Approximately 500 g of each feedstock having the composition shown in Table 1 was melted by heating and was then cooled for crystallization, thereby forming a slurry containing crystals. These slurries thus formed were each fed into a high pressure crystallization vessel (model 50) so as to conduct pressure crystallization for separation/purification, thereby yielding products (cakes containing 2,6-DMN). Cooling temperatures, pressures during crystallization, and compositions of the products are also shown in Table 1.

TABLE 1

| Sample # | | 1 | 2 | 3 | 4 | 5 | 6 |
|---|---|---|---|---|---|---|---|
| Feedstock | 2,6-DMN (%) | 74.5 | 83.7 | 93.5 | 84.5 | 79.7 | 70.9 |
| | 2,7-DMN (%) | 3.4 | 5.6 | 5.5 | 8.2 | 9.9 | 10.0 |
| | Others (%) | 22.1 | 10.7 | 1.0 | 7.3 | 10.4 | 19.0 |
| Cooling Temperature (° C.) | | 93 | 101 | 100 | 101 | 88 | 88 |
| Pressure during Crystallization (MPa) | | 150 | 150 | 150 | 200 | 200 | 200 |
| Product | 2,6-DMN (%) | 99.0 | 99.2 | 99.2 | 97.8 | 97.5 | 96.5 |
| | 2,7-DMN (%) | 0.7 | 0.8 | 0.7 | 1.7 | 2.3 | 3.2 |
| | Others (%) | 0.35 | 0.04 | 0.09 | 0.50 | 0.19 | 0.37 |
| Recovery Rate of 2,6-DMN (%) | | 31 | 30 | 39 | 34 | 21 | 29 |

Figure 4:
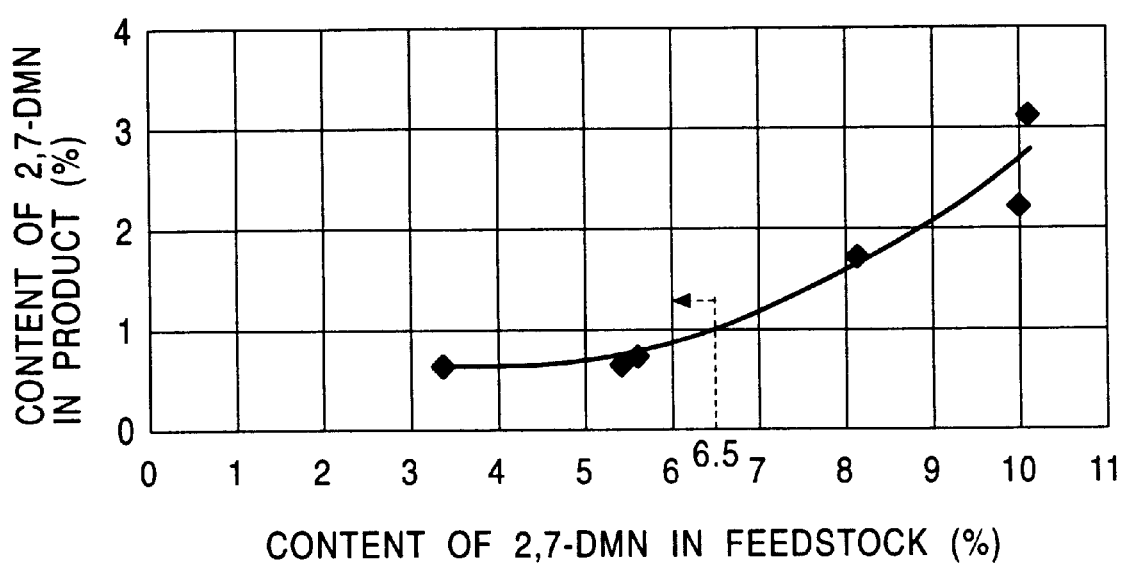
FIG. 4 is a graph showing the relationship between the content of 2,7-DMN in a feedstock and the content of 2,7-DMN in a product obtained by separation/purification.

Among the results shown in Table 1, the relationship between the content of 2,7-DMN in the feedstock and the content of 2,7-DMN in the product obtained by separation/purification is shown in FIG. 4. From the relationship shown in FIG. 4, it was understood that in order to obtain a 2,6-dimethylnaphthalene having a purity of 99% or more, the content of the 2,7-DMN in the feedstock had to be 6.5% or less and was preferably 6% or less.

Second Example (First and Second Cases According to the Present Invention, and First Comparative Example)

After approximately 350 g of a feedstock A (a mixture containing DMN isomers) having the composition shown in Table 2 was heated to 50° C. and was maintained for 30 minutes so that every crystal was melted, the molten feedstock A was cooled to temperatures (26° C., 18° C., and 0° C.) shown in Table 2, respectively, so that crystals were precipitated. The slurries containing crystals thus formed were processed by press filtration at a pressure of approximately 10 MPa, whereby cakes containing DMN isomers and mother liquors having the compositions shown in Table 2 were obtained.

present invention except that a feedstock B having a different composition from the feedstock A was used. In this comparative example, the temperature during crystallization was decreased to 30° C. The results are shown in Table 3.

TABLE 3

| Conditions for Crystallization and Solid-Liquid Separation | Crystallization Method | Second Comparative Example Cooling Crystallization | |
|---|---|---|---|
| | Temperature for Crystallization | 30° C. | |
| | Solid-Liquid Separation Method | Press Filtration at 10 MPa | |
| Result of | Yield of Cake (%) | 19 | |
| Separation (%) | Component | Feedstock B (%) | Cake | Mother Liquor |
| | 2,6-DMN | 29.83 | 82.33 | 16.17 |
| | 2,7-DMN | 15.52 | 7.53 | 18.64 |
| | Impurities | 54.65 | 10.14 | 65.19 |
| | C2,6/C2,7 | 1.92 | 10.93 | 0.87 |

In the second comparative example, the ratio (C2,6/C2,7) of the content of the 2,6-DMN in the mother liquor to that of the 2,7-DMN therein was also 1.0 or less, and the content

TABLE 2

| | | | Case 1 of the Present Invention | | Case 2 of the Present Invention | | First Comparative Example | |
|---|---|---|---|---|---|---|---|---|
| Conditions for Crystallization and Solid-Liquid Separation | Crystallization Method | | Cooling Crystallization | | Cooling Crystallization | | Cooling Crystallization | |
| | Temperature for Crystallization | | 26° C. | | 18° C. | | 0° C. | |
| | Solid-Liquid Separation Method | | Press Filtration at 10 MPa | | Press Filtration at 10 MPa | | Press Filtration at 10 MPa | |
| Result of | Yield of Cake (%) | | 9.7 | | 14.8 | | 22.8 | |
| Separation (%) | Component | Feedstock A (%) | Cake | Mother Liquor | Cake | Mother Liquor | Cake | Mother Liquor |
| | 2,6-DMN | 21.95 | 76.52 | 15.74 | 68.21 | 13.16 | 68.31 | 8.43 |
| | 2,7-DMN | 10.45 | 4.49 | 11.43 | 5.92 | 10.68 | 7.57 | 11.1 |
| | Other DMN's | 54.46 | 13.24 | 58.76 | 20.89 | 60.86 | 20.41 | 63.98 |
| | Impurities | 13.14 | 5.75 | 14.07 | 4.98 | 15.30 | 3.71 | 16.49 |
| | C2,6/C2,7 | 2.10 | 17.04 | 1.38 | 11.52 | 1.23 | 9.02 | 0.76 |

According to the results of the first and the second cases of the present invention, the ratio of the content of the 2,6-DMN in the mother liquor to that of the 2,7-DMN therein was 1.0 or more, the content of the 2,6-DMN in the cake was 60% or more, and the content of the 2.7-DMN in the cake was 6.5% or less, whereby the content of the 2,6-DMN in the cake could be 99% or more after separation/purification was performed. In contrast, in the first comparative example, the content of the 2,7-DMN in the cake was more than 6.5%, and hence, the content of the 2,6-DMN could not be 99% or more even after separation/purification was performed. In addition, the recovery rate of the 2,6-DMN in the second case of the present invention was 46%.

Second Comparative Example

Crystallization and solid-liquid separation were performed in a manner equivalent to that in the first case of the of the 2,7-DMN in the cake thus obtained was also more than 6.5%, whereby, as in the first comparative example, the content of the 2,6-DMN in the cake could not be 99% or more even after separation/purification was performed.

Third Example

The mother liquor obtained in the second case of the present invention was used as a feedstock C, cooling was again performed to 0° C., and solid-liquid separation was then performed. The results are shown in Table 4. In this solid-liquid separation step, both press filtration at a pressure of 10 MPa as in the first case of the present invention and pressure filtration at an air pressure of 0.2 MPa were performed, respectively.

TABLE 4

| Conditions for Crystallization and Solid-Liquid Separation | | | Third Example | | | |
|---|---|---|---|---|---|---|
| | Crystallization Method | | Cooling Crystallization | | Cooling Crystallization | |
| | Temperature for Crystallization | | 0° C. | | 0° C. | |
| | Solid-Liquid Separation Method | | Press Filtration at 10 MPa | | Pressure Filtration at 0.2 MPa | |
| Result of | Yield of Cake (%) | | 7.0 | | 15 | |
| Separation (%) | Component | Feedstock C (%) | Cake | Mother Liquor | Cake | Mother Liquor |
| | 2,6-DMN | 13.16 | 68.6 | 8.43 | 34.46 | 8.54 |
| | 2,7-DMN | 10.68 | 12.41 | 11.1 | 11.38 | 11.21 |
| | Other DMN's | 60.86 | 15.79 | 63.98 | 44.11 | 63.99 |
| | Impurities | 15.30 | 3.20 | 16.49 | 10.05 | 16.26 |
| | C2,6/C2,7 | 1.23 | 5.53 | 0.76 | 3.03 | 0.76 |

As shown in Table 4, it was understood that each of the cakes obtained by both solid-liquid separation methods described above contained 2,6-DMN at a high content and, in addition, that each ratio (C2,6/C2,7) of the content of the 2,6-DMN to that of the 2,7-DMN was higher than that of the feedstock A.

Next, after the cake (feedstock D) obtained by the pressure filtration was again melted by heating to 80° C., crystallization was performed by cooling to 37° C., and subsequently, solid-liquid separation by press filtration at a pressure of 10 MPa was conducted. The results are shown in Table 5.

TABLE 5

| Conditions for Crystallization and Solid-Liquid Separation | | | Third Example Cooling Crystallization | |
|---|---|---|---|---|
| | Crystallization Method | | | |
| | Temperature for Crystallization | | 37° C. | |
| | Solid-Liquid Separation Method | | Press Filtration at 10 MPa | |
| Result of | Yield of Cake (%) | | 24.0 | |
| Separation (%) | Component | Feedstock D (%) | Cake | Mother Liquor |
| | 2,6-DMN | 34.46 | 87.5 | 17.72 |
| | 2,7-DMN | 11.38 | 4.5 | 13.3 |

TABLE 5-continued

| Other DMN's | 44.11 | 6.70 | 56.30 |
| Impurities | 10.05 | 1.30 | 12.68 |
| C2,6/C2,7 | 3.03 | 19.44 | 1.33 |

A cake containing 87.5% of 2,6-DMN and 4.5% of 2,7-DMN was obtained. By combining the procedure in the second example with that in the third example, that is, by repeating the cooling crystallization and the solid-liquid separation, the recovery rate of the 2,6-DMN after separation/purification was increased to 50% from 46% which was obtained only by the procedure in the second example.

Figure 5:
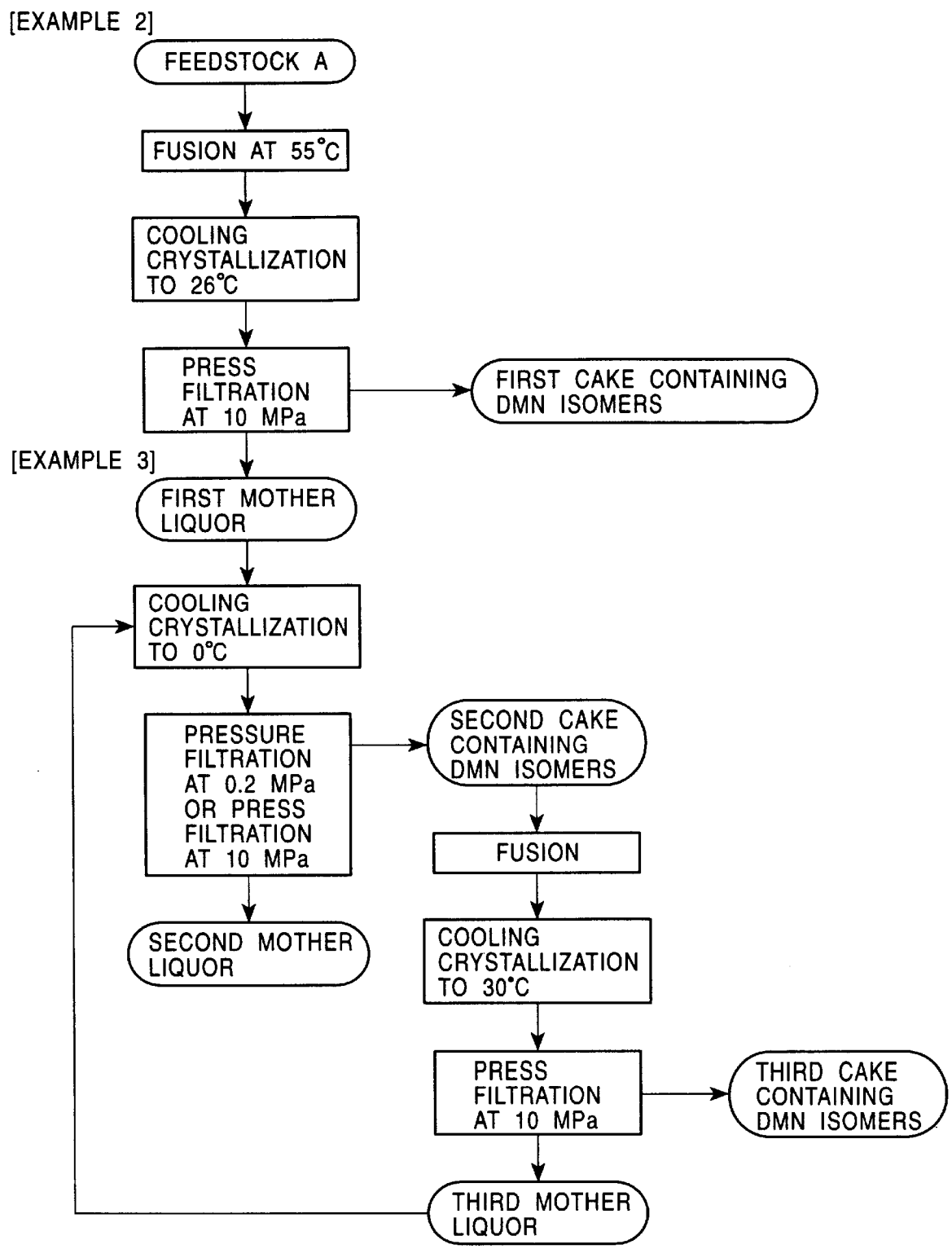
FIG. 5 is a flowchart showing continuous condensation steps described in a third example.

In addition, when the crystallization and solid-liquid separation were repeated in accordance with the continuous condensation flow shown in FIG. 5, the recovery rate of the 2,6-DMN with respect to the feedstock A could be increased to 66%.

Third Comparative Example

In the third comparative example, a feedstock E was crystallized so that the content ratio of the 2,6-DMN to that of the 2,7-DMN in the mother liquor was 1.0 or less, and the results are shown in Table 6.

TABLE 6

| Conditions for Crystallization and Solid-Liquid Separation | | | Third Comparative Example | | | |
|---|---|---|---|---|---|---|
| | Crystallization Method | | Cooling Crystallization | | Cooling Crystallization | |
| | Temperature for Crystallization | | 30° C. | | 18° C. | |
| | Solid-Liquid Separation Method | | Press Filtration at 10 MPa | | Pressure Filtration at 0.2 MPa | |
| Result of | Yield of Cake (%) | | 6.6 | | 15 | |
| Separation (%) | Component | Feedstock E (%) | Cake | Mother Liquor | Cake | Mother Liquor |
| | 2,6-DMN | 21.37 | 70.50 | 17.68 | 52.60 | 13.09 |
| | 2,7-DMN | 21.08 | 13.67 | 21.79 | 27.53 | 19.41 |

TABLE 6-continued

|  | Third Comparative Example | | | | |
|---|---|---|---|---|---|
| Impurities | 57.55 | 15.83 | 60.53 | 19.87 | 67.50 |
| C2,6/C2,7 | 1.01 | 5.16 | 0.81 | 1.91 | 0.67 |

As shown in Table 6, the content of the 2,7-DMN in the cake containing DMN isomers was considerably increased to more than 6.5%, and in particular, when the ratio 2,6-DMN/2,7-DMN in the mother liquor was 0.7 or less, it was understood that a larger amount of 2,7-DMN was present in the cake.

Fourth Example

After 10 kg of a mixed feedstock containing 2,6-DMN shown in Table 7 was melted by heating to 60° C. or more, crystallization was performed by cooling to 39.5° C., so that crystals were precipitated. This slurry containing the crystals thus obtained was processed by pressure filtration at an air pressure of 0.2 MPa, whereby a cake 4-1 containing DMN isomers and a mother liquor 4-1 were obtained.

Next, 3 kg of the cake 4-1 was totally melted at 80° C. and was then crystallized by cooling to 39.5° C., so that crystals were precipitated. This slurry containing crystals thus formed was processed by press filtration at a pressure of 10 MPa, whereby a cake 4-2 containing DMN isomers and a mother liquor 4-2 were obtained.

In addition, after approximately 400 g of the cake 4-2 was totally melted at 110° C., the melted cake was fed into a high pressure crystallization vessel (model 50), separation/purification was performed by high pressure crystallization at a pressure of 120 MPa, whereby a cake 4-3 composed of 99% or more of 2,6-DMN and a mother liquor 4-3 were obtained. The recovery rate of the 2,6-DMN obtained by these pressure filtration, press filtration, and high pressure crystallization was 27.7% with respect to the feedstock 4-1.

Subsequently, the mother liquor 4-1 and the mother liquor 4-2 were mixed together so as to form a feedstock F-4 shown in Table 8, and this feedstock was totally melted by heating to 50° C. or more and was then crystallized by cooling to 17° C., so that crystals were precipitated. This slurry containing the crystals thus formed was processed by pressure filtration at an air pressure of 0.2 MPa, whereby a cake 4-4 containing DMN isomers and a mother liquor 4-4 were obtained.

TABLE 8

| Crystallization Method | Cooling Crystallization | | |
|---|---|---|---|
| Temperature for Crystallization | 17° C. | | |
| Solid-Liquid Separation Method | Pressure Filtration at 0.2 MPa | | |
| Result of | Yield of Cake (%) | 28 | | |
| Separation (%) | | Feedstock F-4 (Mother Liquor 4-1 + Mother Liquor 4-2) | Cake 4-4 | Mother Liquor 4-4 |
| | Component | | | |
| | 2,6-DMN | 19.1 | 33.0 | 11.7 |
| | 2,7-DMN | 14.8 | 15.3 | 16.7 |
| | Impurities | 66.1 | 51.7 | 71.6 |
| | C2,6/C2,7 | 1.3 | 2.2 | 0.7 |

Because of similar procedures for separating 2,6-DMN, the cake 4-4 had a composition approximately equivalent to that of the cake 4-1, and hence, it was understood that the cake 4-4 could be recovered as an intermediate feedstock from which a 2,6-DMN crystal having a purity of 99% or more could be obtained.

Furthermore, when the cake 4-4 and the mother liquor 4-3 were mixed together, a mixed feedstock F-5 shown in Table 9 was obtained, and by adding the feedstock F-1 thereto so that the ratio F-5/F-1 was 58/42, a feedstock F-6 having the composition shown in Table 9 was obtained.

TABLE 7

| Crystallization Method | | Cooling Crystallization | | | Cooling Crystallization | | | High Pressure Crystallization | | |
|---|---|---|---|---|---|---|---|---|---|---|
| Temperature for Crystallization | | 39.5° C. | | | 39.5° C. | | | 100° C. | | |
| Solid-Liquid Separation Method | | Pressure Filtration at 0.2 MPa | | | Press Filtration at 10 MPa | | | High Pressure Crystallization at 120 MPa | | |
| Result of Separation | Yield of Cake (%) | 44 | | | 30 | | | 59 | | |
| (%) | Component | Feedstock F-1 | Cake 4-1 | Mother Liquor 4-1 | Feedstock F-2 (Cake 4-1) | Cake 4-2 | Mother Liquor 4-2 | Feedstock F-3 (Cake 4-2) | Cake 4-3 | Mother Liquor 4-3 |
| | 2,6-DMN | 28.1 | 39.6 | 19.0 | 39.6 | 87.8 | 19.2 | 87.8 | 99.35 | 71.5 |
| | 2,7-DMN | 13.4 | 12.4 | 14.2 | 12.4 | 4.0 | 16.0 | 4.0 | 0.48 | 8.3 |
| | Impurities | 58.5 | 48.0 | 66.8 | 48.0 | 8.2 | 64.8 | 8.2 | 0.17 | 20.2 |
| | C2,6/C2,7 | 2.1 | 3.2 | 1.3 | 3.2 | 22.2 | 1.20 | 22.2 | 208 | 8.59 |

TABLE 9

| Component | Feedstock F-5 (%) (Mother Liquor 4-3 + Cake 4-4) | Feedstock F-6 (%) (Mother Liquor 4-5: Cake 4-1 = 58:42) |
|---|---|---|
| 2,6-DMN | 39.9 | 34.0 |
| 2,7-DMN | 14.1 | 13.7 |
| Impurities | 46.0 | 52.3 |
| C2,6/C2,7 | 2.8 | 2.5 |

The feedstock F-6 was processed by press filtration in a manner similar to that for the feedstock F-2, so that a cake 4-6 and a mother liquor 4-6 were obtained. The results are shown in Table 10.

TABLE 10

| Crystallization Method Temperature for Crystallization Solid-Liquid Separation Method | Cooling Crystallization 37° C. Press Filtration at 10 MPa | | |
|---|---|---|---|
| | Result of Separation (%) | | |
| Yield of Cake (%) Component | Feedstock F-6 (%) | Cake 4-6 | Mother Liquor 4-6 |
| | | 25 | |
| 2,6-DMN | 34.0 | 87.5 | 17.5 |
| 2,7-DMN | 13.7 | 4.4 | 16.1 |
| Impurities | 52.3 | 8.1 | 66.4 |
| C2,6/C2,7 | 2.5 | 19.8 | 1.1 |

It was understood that when the cake 4-6 was processed in a manner similar to that for the cake 4-2, a 2,6-DMN crystal having a purity of 99% or more could be obtained, and that when the mother liquor 4-6 was processed in a manner similar to that for the mother liquor 4-2, the mother liquor 4-6 could be partly recovered as an intermediate feedstock from which a 2,6-DMN having a purity of 99% or more could be obtained.

Figure 6:
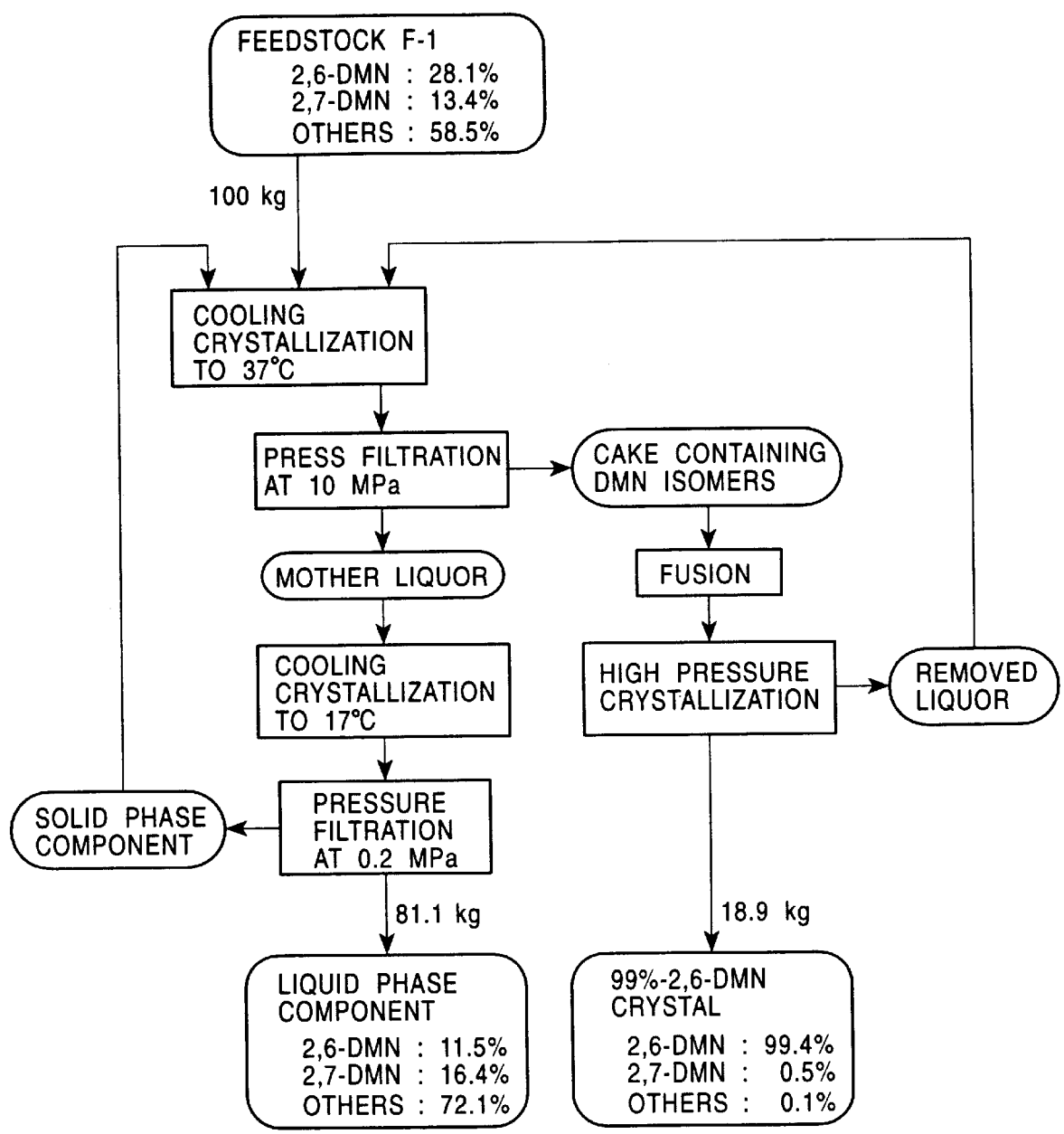
FIG. 6 is a flowchart showing continuous condensation steps described in a fourth example.

As a result, by continuous condensation and purification flow shown in FIG. 6, a 2,6-DMN crystal having a purity of 99% or more could be obtained in a high yield. In the case described above, the recovery rate of the 2,6-DMN with respect to the feedstock F-1 was 66.9%. However, the result of this example was described by way of example, and hence, the present invention is not limited thereto.

Fifth Example

A feedstock G shown in Table 8 was melted by heating to 50° C. or more and was then cooled to 37° C., whereby crystals were precipitated. In this slurry containing the crystals thus formed, the ratio of the content of the 2,6-DMN to that of the 2,7-DMN was 1.2. This slurry containing the crystals was processed by press filtration at various pressures shown in Table 11. The analytical results of the cakes thus formed are shown in Table 11.

TABLE 11

| Crystallization Method Temperature for Crystallization Solid-Liquid Separation Method | | | Cooling Crystallization 37° C. Press Filtration | | | | | |
|---|---|---|---|---|---|---|---|---|
| Pressure for Press Filtration Result of | Component | Feedstock | Mother | 1 MPa Cake | 2 MPa Cake | 3 MPa Cake | 7 MPa Cake | 10 MPa Cake |
| Separation (%) | | G (%) | Liquor | 5-1 | 5-2 | 5-3 | 5-4 | 5-5 |
| | 2,6-DMN | 33.9 | 18.8 | 74.4 | 78.1 | 80.2 | 86.7 | 86.5 |
| | 2,7-DMN | 13.3 | 16.0 | 6.5 | 5.8 | 5.5 | 5.2 | 4.4 |
| | Impurities | 52.8 | 65.2 | 19.1 | 16.1 | 14.3 | 8.1 | 9.1 |
| | C2,6/C2,7 | 2.5 | 1.2 | 11.4 | 13.3 | 14.6 | 16.6 | 19.7 |

It was understood from the results shown in Table 11 that the pressure for press filtration was preferably 2 MPa or more in order to obtain a 2,6-DMN having a purity of 99% or more.

Fourth Comparative Example

A feedstock (a mixture containing DMN isomers) having the composition shown in Table 12 was crystallized by cooling to 9° C. and was then processed by press filtration at approximately 100 kg/cm$^2$, whereby a cake containing DMN isomers and having the composition shown in Table 12 was obtained. This cake containing DMN isomers in an amount of 100 g and normal hexane in an amount of 200 g were fed into a separable flask provided with a stirrer and were then stirred at 30° C. for 1 hour. Subsequently, after the crystals were separated by suction filtration, 100 g of a pure solvent was added thereto. The crystal thus formed was analyzed using gas chromatography, and a crystal having the composition shown in Table 12 was obtained.

TABLE 12

| Component (wt%) | Feedstock | Cake by Cooling Crystallization and Press Filtration | Mother Liquor by Cooling Crystallization and Press Filtration | Crystal after Washing (Fourth Comparative Example) |
|---|---|---|---|---|
| 2,6-DMN | 11.68 | 75.72 | 9.30 | 97.66 |
| 2,7-DMN | 12.03 | 10.54 | 12.09 | 2.34 |
| Other DMN Isomers | 26.23 | 6.01 | 6.01 | Below detection limit |
| Impurities | 50.06 | 7.93 | 7.93 | Below detection limit |
| Total | 100.00 | 100.00 | 100.00 | 100.00 |

In the fourth comparative example in which washing was performed for a cake containing 6.5% or more of the 2,7-DMN, a highly pure 2,6-DMN having a purity of 99% or more could not be obtained.

Sixth Example

Cakes containing DMN isomers and mother liquors having the compositions shown in Table 13 were obtained in a manner similar to that in the fourth comparative example except that a feedstock having the composition shown in Table 13 was crystallized by cooling to 15° C. in a first stage and was then crystallized by cooling to 70° C. in a second stage, and that press filtration was preformed at approximately 100 kg/cm$^2$ after each cooling crystallization was performed.

TABLE 13

| Component (wt %) | Feedstock | Cake after First Stage Cooling Crystallization | Mother Liquor after First Stage Cooling Crystallization | Cake after Second Stage Cooling Crystallization | Mother Liquor after Second Stage Cooling Crystallization | Crystal after Washing (Sixth Example) |
|---|---|---|---|---|---|---|
| 2,6-DMN | 11.68 | 58.00 | 11.21 | 80.04 | 52.61 | 99.16 |
| 2,7-DMN | 12.03 | 6.00 | 12.09 | 4.92 | 6.28 | 0.80 |
| Other DMN Isomers | 26.23 | 15.00 | 26.34 | 13.36 | 15.44 | Below detection limit |
| Impurities | 50.06 | 21.00 | 50.35 | 2.58 | 25.66 | 0.04 |
| Total | 100.00 | 100.00 | 100.00 | 100.00 | 100.00 | 100.00 |

In the sixth example in which washing was performed for a cake containing 60% or more of 2,6-DMN and 6.5% or less of 2,7-DMN, a highly pure 2,6-DMN crystal having a purity of 99% or more could be obtained. In addition, the yield of the highly pure 2,6-DMN with respect to the 2,6-DMN in the cake before washing was 65.05%. According to the present invention, it was understood that a highly pure 2,6-DMN could be obtained in a high recovery rate.

What is claimed is:

1. A method for manufacturing 2,6-dimethylnaphthalene comprising:

performing at least one crystallization and at least one solid-liquid separation of a liquid comprising dimethylnaphthalene isomers used as a feedback so that the liquid is separated into a cake comprising dimethylnaphthalene isomers and a mother liquor, and so that the content of 2,6-dimethylnaphthalene in the cake is increased relative to the content of 2,6-dimethylnaphthalene in the liquid feedstock; and performing separation/purification of the cake;

wherein the crystallization and the solid-liquid separation are performed under the condition in which the ratio of the content of 2,6-dimethylnaphthalene in the mother liquor to that of 2,7-dimethylnaphthalene therein is not less than 1 so that the content of 2,6-dimethlylnaphthalene in the cake is 60 wt % or more and that the content of 2,7-dimethylnaphthalene therein is 6.5 wt % or less, whereby a 2,6-dimethylnaphthalene having a purity of 99% or more is obtained by performing the separation/purification of the cake.

2. The method according to claim 1, wherein the feedback is a liquid comprising 5 wt % or more of 2,7-dimethylnaphthalene.

3. A method according to claim 1, wherein, in the performing the crystallization and the solid-liquid separation, cooling crystallization is performed, and press filtration is then performed.

4. A method according to claim 2, wherein, in the performing the crystallization and the solid-liquid separation, cooling crystallization is performed, and press filtration is then performed.

* * * * *